United States Patent [19]
Eddleman et al.

[11] 4,301,118
[45] Nov. 17, 1981

[54] PROTEIN CONCENTRATOR

[75] Inventors: Roy T. Eddleman, Beverly Hills, Calif.; Gregory F. Moran, Monrovia, both of Calif.

[73] Assignee: Spectrum Medical Industries, Inc., Los Angeles, Calif.

[21] Appl. No.: 127,899

[22] Filed: Mar. 6, 1980

[51] Int. Cl.³ .................... B01L 11/00; B01L 3/00; B01D 13/00
[52] U.S. Cl. ............................. 422/101; 23/230 B; 210/321.1; 210/905; 210/927
[58] Field of Search .................... 210/321.1, 905, 927; 422/99, 101, 102

[56] References Cited
U.S. PATENT DOCUMENTS 3,414,131 12/1968 Allen, Jr. .................... 141/65 X
3,969,250 7/1976 Farr ............................ 210/927 X Primary Examiner—Michael S. Marcus
Attorney, Agent, or Firm—Edgar W. Averill, Jr.

[57] ABSTRACT

A protein concentrator having a reservoir for holding a protein solution and a membrane positioned within the protein solution through which a portion of the solution passes. The membrane is held in the walls of a container assembly and a water soluble polymer is located on one side of the membrane to increase the concentration gradient through the membrane for concentrating the solution.

11 Claims, 6 Drawing Figures

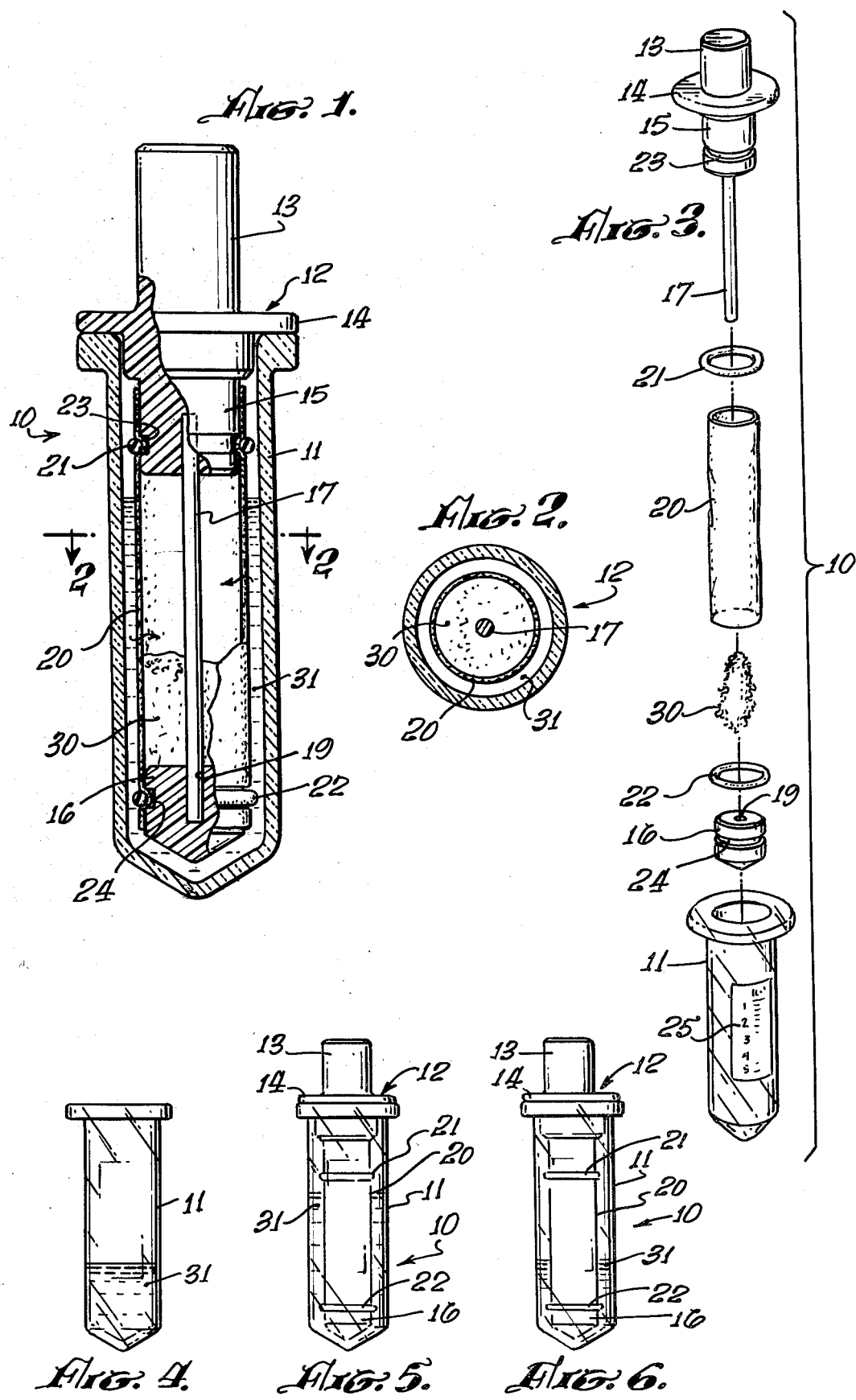

PROTEIN CONCENTRATOR

BACKGROUND OF THE DISCLOSURE

The field of the invention is medical or laboratory apparatus, and the invention relates more specifically to devices for concentrating solutions.

In many laboratory analysis, it is necessary to increase the concentration of a sample so that a meaningful and efficient laboratory test may be performed. For instance, in urinalysis the majority of the specimen consists of salts and water that are not significant to the test to be run and instead ingredients such as proteins are of clinical interest, but, because of their dilution are difficult to study.

There is thus a need to concentrate various solutions and particularly protein solutions. One common technique for carrying out this step is referred as ultra-filtration where the protein solution is forced through a semi-permeable membrane by a pressure gradient created by vacuum, centrifugation or pressure. Such procedures are both time consuming and require relatively expensive equipment. With the importance of eliminating cross contamination, it would be further beneficial if a procedure could be devised which utilized disposable apparatus.

SUMMARY OF THE INVENTION

It is thus an object of the present invention to provide a protein concentrator which is efficient and inexpensive.

The present invention is for a protein concentrator having a reservoir for holding a protein solution. A container is held within the reservoir and a semi-permeable membrane is supported by the container and positioned in the wall thereof so that a protein solution held within the reservoir will contact the outer surface of the semi-permeable member. The semi-permeable member has openings large enough to permit the passage of water but has a molecular weight cut-off such as to prohibit the passage of at least some of the constituents of the protein solution. The inner surface of the semi-permeable member is exposed to the interior of the container and a water soluble, non-ionic polymeric powder is held within the container adjacent to at least a portion of the semi-permeable member. The polymeric powder has a molecular size such that it will not pass through the semi-permeable member. Preferably, the container is cylindrical and the reservoir is cylindrical so that when the container is inserted in the reservoir, the protein solution is held in the annular space between the reservoir and container. When a protein solution is placed in the reservoir and the container is inserted, the protein solution rises in the annular space and contacts the outer surface of the semi-permeable membrane. The semi-permeable membrane allows the passage of water therethrough and when water begins to pass through the membrane, it begins to dissolve the water soluble non-ionic polymer held within the container. This creates a highly concentrated polymeric solution which in turn results in a concentration imbalance across the membrane thereby increasing the flux of protein solution through the membrane and speeding the concentration process. The polymeric powder is made from a polymer having a molecular size so that it will not pass through the semi-permeable membrane.

BRIEF DESCRIPTION OF THE DRAWINGS

FIG. 1 is a side-elevational view partly broken away of the protein concentrator of the present invention.

FIG. 2 is a cross-sectional view taken along line 2—2 of FIG. 1.

FIG. 3 is an exploded perspective view of the protein concentrator of FIG. 1.

FIG. 4 is a side-elevational view of the reservoir of the protein concentrator of FIG. 1.

FIG. 5 is a side-elevational view of the reservoir and container of the protein concentrator of FIG. 1.

FIG. 6 is side-elevational view of the reservoir and container of the protein concentrator of FIG. 1.

DESCRIPTION OF THE PREFERRED EMBODIMENTS

A protein concentrator 10 is shown in side-elevational view in FIG. 1. Concentrator 10 has a reservoir 11 which may be fabricated from any suitable material such as clear polystyrene or glass. It is beneficial and preferred that reservoir 11 be made from a generally transparent substance so that the degree of concentration may be readily observed. A polymer containing assembly generally indicated by reference character 12 has a handle 13, a lip 14 an upper cylindrical member 15 and a lower cylindrical member 16. Upper cylindrical member 15 is held to a lower cylindrical member 16 by a finger or rib 17. The articles referred to by reference characters 12 through 17 may be fabricated from any suitable substance which is inert to the protein solutions to be concentrated and preferably is made from a polymeric material such as clear polystyrene. In the preferred embodiment, the device is disposable and ease of fabrication by injection molding and extruding is desirable. In the event a reusable device is desired, other consideration such as the ability to withstand the purification techniques is, of course, necessary.

A semi-permeable membrane 20 is formed from a flexible tube of regenerated cellulose which is held to members 15 and 16 by a pair of O-rings 21 and 22 which cooperate with grooves 23 and 24 respectively. O-ring 22 in addition to forming a very efficient and watertight seal between membrane 20 and cylindrical member 16 also tends to increase the agitation of the protein solution in a manner described more fully below.

A water soluble polymer 30 is held within the polymer container assembly 12 by the semi-permeable membrane 20 and performs an important function in the practice of the present invention as described below. A protein solution 31 is held in the annular space between reservoir 11 and membrane 20 and passes through membrane 20 in the direction of the arrows shown both in FIGS. 1 and 2.

The components of the protein concentrator are shown in exploded view in FIG. 3. In the particular embodiments shown, the handle 13 is formed integrally with lip 14 and upper cylindrical member 15. There is an opening along the axis of handle 13 into which finger 17 is inserted and held by friction. The lower cylindrical member 16 has a hole 19 into which finger 17 is inserted and held by friction.

In assembling the container, O-ring 21 is placed over upper cylindrical member 15 and finger 17 is inserted in handle 13. The semi-permeable membrane tube 20 is then placed over upper cylindrical member 15 and O-ring 21 is rolled down into groove 23 thereby holding the upper end of semi-permeable membrane 20 against upper cylindrical member 15. A measured quantity of water soluble polymer powder 30 is then placed within the inverted semi-permeable membrane 20 and lower cylindrical member 16 is inserted over finger 17. The open end of tube 20 is then placed over lower cylindrical member 16 and O-ring 22 is placed around the exterior of membrane 20 adjacent the groove 24. It is useful that a label 25 or other form of marking be placed on the exterior of reservoir 11 so that the user may have some measurement of the flow of water through membrane 20.

In practice, a measured amount of protein solution 31 is placed in reservoir 11 as shown in FIG. 4. The amount of solution should be such that when the container assembly 12 is inserted in the reservoir 11 as shown in FIG. 5, the solution does not overflow the reservoir. The solution 31 rises along the outer surface of membrane 20 and since membrane 20 is chosen from a material which is permeable to a portion of solution 31, a flow of liquid occurs through membrane 20. In the case of aqueous solutions, this flow is water and dissolved molecular species which are small enough to pass through the pore of the membrane. Since protein molecules tend to be quite large, it is possible to select semi-permeable membranes which have a molecular weight cut-off which do not permit the flow of protein molecules therethrough and thus the protein solution is concentrated by this selective flux. Once the water and other small molecules have passed through membrane 20, it begins to dissolve water soluble polymer 30 resulting in a highly concentrated solution within membrane 20. Since the concentration of water soluble matter is greater on the inside of membrane 20, there is a tendency to increase the flux or flow of water through the membrane walls in an attempt to equalize the salt concentrations on both sides of the membrane. It is important that the molecular size of the water soluble polymer 30 be selected such that it cannot pass through the pores of semi-permeable membrane 20 thereby retaining the high concentration within the container 12 to greatly speed the flow of water out of protein solution 30 thereby concentrating the same.

Another very important feature of the present invention is the method which may be used to agitate the protein solution 31 in the annular area between the membrane and the reservoir. This may be done simply by lifting handle 13 which causes the protein solution to flow around lower cylindrical member 16 thereby stirring the solution. The presence of O-ring 22 further enhances this stirring action. It is preferable that lower cylindrical member 16 be positioned to such that it about touches the bottom of the reservoir 11 so that a large proportion of the protein solution is held in the annular space adjacent semi-permeable membrane 20. As the protein solution becomes more concentrated, the level of the protein solution becomes more concentrated, the level of the protein solution in the annular space decreases as shown in FIG. 6 and the extent of this decrease may be measured by observation of label 25 or by simply observing the level.

The selection of the water soluble polymer forms an important aspect of the present invention. In addition to its requirements of water solubility and molecular size, it is also important that the polymer not interfere with the flow of liquid through the semi-permeable membrane. It has been found that non-ionic polymers such as polyvinyl pyrrilidone performs this function satisfactorily. The material of construction of the semi-permeable membrane while an important feature of the present invention is well known to those skilled in the art and the particular selection of a preferred membrane will be depended upon the nature of the protein solution to be concentrated. Regenerated cellulose is particularly useful for many medical laboratory techniques relating to urinalysis.

While a cylindrical reservoir and membrane have been shown, other shapes may of course be used. It is beneficial, however, that a relatively narrow annular space exist between the container and the reservoir so that there is a relatively high surface area exposed to the protein solution to be concentrated. The container assembly should displace at least 50% of the original specimen and preferably 90%.

The present embodiments of this invention are thus to be considered in all respects as illustrative and not restrictive; the scope of the invention being indicated by the appended claims rather than by the foregoing description. All changes which come within the meaning and range of equivalency of the claims therefore are intended to be embraced therein.

What is claimed is:

1. A protein concentrator, comprising:
    means defining a reservoir for holding a protein solution;
    a cover assembly held within said reservoir;
    a semi-permeable membrane member having openings large enough to permit passage of water but having a molecule weight cut-off sufficient to prohibit the passage of at least some of the consituents of a protein solution, said membrane member being supported by said cover assembly and forming a tubular container positioned within the reservoir so that a protein solution held within the reservoir will contact the outer surface of the semi-permeable member and the inner surface of the semi-permeable member will not be exposed to the contents of the reservoir, the semi-permeable member being sealed to the container to prevent any portion of the protein solution from passing to the interior of the container without passing through the member; and
    a water soluble polymeric powder held within said membrane, said polymeric powder having a molecular size so that it will not pass through the semi-permeable membrane member, whereby when a protein solution is placed in the reservoir, the protein solution will contact the exterior surface of the semi-permeable membrane and a portion of the protein solution will pass through the membrane and dissolve a portion of the water soluble polymeric powder creating a concentration gradient across the membrane to increase the flux of the solution through the membrane and into the container thereby concentrating the protein solution in the reservoir.

2. The protein concentrator of claim 1 wherein said reservoir is cylindrical.

3. The protein concentrator of claim 1 wherein said container and said reservoir are cylindrical.

4. The protein concentrator of claim 1 wherein the lower cylindrical member about touches the bottom of the reservoir when the container is placed in said reservoir.

5. The protein concentrator of claim 4 wherein the container displaces at least 50% of the interior of the reservoir.

6. The protein concentrator of claim 1 wherein the container comprises a lower cylinder and an upper cylinder held apart by a finger member and the semi-permeable membrane comprises a tubular sleeve surrounding at least a portion of the upper cylinder and the lower cylinder.

7. The protein concentrator of claim 6 wherein the lower cylinder has an annular groove in the exterior surface thereof and the semi-permeable membrane member is held to the lower cylinder by an O-ring.

8. The protein concentrator of claim 6 wherein the upper cylinder has an annular groove in the exterior surface thereof and the semi-permeable membrane member is held to the upper cylinder member by an O-ring.

9. The protein concentrator of claim 1 wherein said semi-permeable membrane in a tubular member made from regenerated cellulose.

10. The protein concentrator of claim 1 wherein said water soluble polymer is a non-ionic water soluble polymer.

11. The protein concentrator of claim 1 wherein said water soluble polymer is polyvinyl pyrrilidone.

* * * * *